United States Patent [19]

Yoshioka et al.

[11] Patent Number: 4,931,455

[45] Date of Patent: Jun. 5, 1990

[54] ALKYLAMINOPYRIMIDINE DERIVATIVE AND INSECTICIDE, ACARICIDE AND FUNGICIDE CONTAINING THE SAME AS ACTIVE INGREDIENT

[75] Inventors: Hirosuke Yoshioka, Wako; Tokio Obata, Ube; Katsutoshi Fujii, Ube; Haruo Yoshiya, Ube; Kiyoshi Tsutsumiuchi, Ube; Shoji Shikita, Ube, all of Japan

[73] Assignees: Ube Industries, Ltd., Ube; Rikagaku Kenkyusho, Wako, both of Japan

[21] Appl. No.: 289,626

[22] Filed: Dec. 22, 1988

[30] Foreign Application Priority Data

Jan. 7, 1988 [JP] Japan .......................... 63-662
Jun. 27, 1988 [JP] Japan .................. 63-156684
Oct. 5, 1988 [JP] Japan .................. 63-249816

[51] Int. Cl.$^5$ ................. A01N 43/54; C07D 239/42; C07D 405/06
[52] U.S. Cl. ................. 514/256; 514/235.8; 514/252; 544/122; 544/295; 544/326; 544/327; 544/328; 544/329
[58] Field of Search ............. 544/326, 327, 328, 329, 544/295, 122; 514/256, 235.8, 252

[56] References Cited

U.S. PATENT DOCUMENTS 4,435,402  3/1984  Tsuji et al. .................. 544/327
4,845,097  7/1989  Matsumoto et al. ............ 544/326

FOREIGN PATENT DOCUMENTS 59-170077  9/1984  Japan .
2135887   9/1984  United Kingdom .

OTHER PUBLICATIONS

Matsumoto, et al., "Chemical Abstracts", vol. 106, 1987, col. 106:14736p.
Yoshioka, et al., "Chemical Abstracts", vol. 109, 1988, col. 109:68866m.

Primary Examiner—Richard L. Raymond
Assistant Examiner—James H. Turnipseed
Attorney, Agent, or Firm—Frishauf, Holtz, Goodman & Woodward

[57] ABSTRACT

There are described an alkylaminopyrimidine derivative represented by the formula:

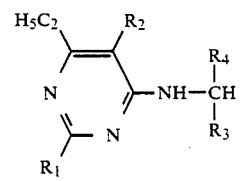

wherein $R_1$ represents a hydrogen atom, a halogen atom, a lower alkyl group, a cycloalkyl group having 3 to 6 carbon atoms, a halogenated lower alkyl group or a substituted or unsubstituted phenyl group; $R_2$ represents a halogen atom; $R_3$ represents a hydrogen atom, a lower alkyl group or a cycloalkyl group having 3 to 6 carbon atoms; and $R_4$ represents a straight or branched alkyl group having 1 to 20 carbon atoms which may have substituents, or an acid addition salt thereof, a process for preparing the same and an insecticide, an acaricide or a fungicide containing the compound as an active ingredient.

52 Claims, No Drawings

ALKYLAMINOPYRIMIDINE DERIVATIVE AND INSECTICIDE, ACARICIDE AND FUNGICIDE CONTAINING THE SAME AS ACTIVE INGREDIENT

BACKGROUND OF THE INVENTION

This invention relates to an alkylaminopyrimidine derivative, a process for producing the same, and an insecticide, an acaricide and a fungicide containing said derivative as the active ingredient.

The alkylaminopyrimidine derivatives of the present invention are novel compound which are not described in any of the literature, etc., and therefore, it has neither been known their biological activities. There is only disclosed an alkylaminoquinazoline derivative represented by the following formula:

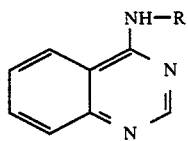

wherein R represents a n-nonyl group, a n-decyl group, a 2-decyl group or a 2-undecyl group, in Japanese Provisional Patent Publication No. 170077/1984.

The aforesaid quinazoline derivative has fungicidal and acaricidal activities, but its effects are insufficient as a fungicidal or acaricidal agent.

SUMMARY OF THE INVENTION

The present inventors have studied to obtain a compound having excellent insecticidal, acaricidal and fungicidal activities than the above known compound, and as the result to accomplish the present invention.

That is, the present invention is to provide a compound represented by the formula (I):

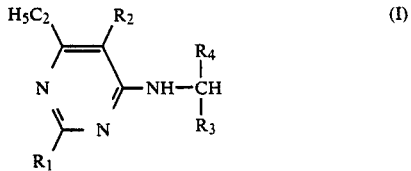

wherein $R_1$ represents a hydrogen atom, a halogen atom, a lower alkyl group, a cycloalkyl group having 3 to 6 carbon atoms, a halogenated lower alkyl group or a substituted or unsubstituted phenyl group; $R_2$ represents a halogen atom; $R_3$ represents a hydrogen atom, a lower alkyl group or a cycloalkyl group having 3 to 6 carbon atoms; $R_4$ represents a straight or branched alkyl group having 1 to 20 carbon atoms which may be substituted by at least one selected from the group consisting of 1 to 3 halogen atoms, an alkoxy group having 1 to 15 carbon atoms, a cycloalkylalkoxy group having 4 to 8 carbon atoms, dioxoranyl group, a lower alkoxyalkoxy group, a hydroxy group, a methoxycarbonyl group, a cycloalkyl group having 3 to 6 carbon atoms, a 2-[2-(lower alkoxy)ethoxy]ethoxy group, a substituted or unsubstituted benzyloxy group, a pyranyloxy group, an imidazol-1-yl group, a triazol-1-yl group, a pyrazol-1-yl group and a substituent Q; where the substituent Q represents $-A-B-R_Q$, in which A represents an oxygen atom or an imino group; B represents a carbonyl group, a thiocarbonyl group or a sulfonyl group; and $R_Q$ represents a lower alkyl group, a cycloalkyl group having 3 to 6 carbon atoms, a halogenated lower alkyl group, an alkoxy group having 1 to 5 carbon atoms, a substituted or unsubstituted phenyl group, a substituted or unsubstituted phenoxy group, a substituted or unsubstituted anilino group, a 2,6-dimethylmorpholin-4-yl group, a 4-methylpiperazin-1-yl group, an imidazol-1-yl group, a triazol-1-yl group, a pyrazol-1-yl group or an amino group substituted by 1 or 2 of lower alkyl groups, or an acid addition salt thereof, a process for preparing the same, and an insecticide, an acaricide and a fungicide containing said derivative as the active ingredient.

DESCRIPTION OF THE PREFERRED EMBODIMENTS

In the above formula (I), the halogen atom may include a fluorine atom, a chlorine atom, a bromine atom and an iodine atom.

The lower alkyl group means a straight or branched alkyl group having 1 to 5 carbon atoms. Such alkyl groups may include a methyl group, an ethyl group, a propyl group, an isopropyl group, a butyl group, an isobutyl group, a sec-butyl group, a t-butyl group, an amyl group, an isoamyl group, a sec-amyl group, a sec-isoamyl group (1,2-dimethylpropyl group) and a t-amyl group (1,1-dimethylpropyl group), etc.

The lower alkoxy group means a straight or branched alkyloxy group and may include, for example, a methoxy group, an ethoxy group, a propoxy group, an isopropoxy group, a butoxy group, an isobutoxy group, a sec-butoxy group, a t-butoxy group, an amyloxy group, an isoamyloxy group, etc.

The cycloalkyl group having 3 to 6 carbon atoms may include a cyclopropyl group, a cyclobutyl group, a cyclopentyl group and a cyclohexyl group.

The halogenated lower alkyl group means those in which one or more of hydrogen atoms of the above lower alkyl group are substituted by the aforesaid halogen atom, and may include, for example, a monochloromethyl group, a dichloromethyl group, a trichloromethyl group, a fluoromethyl group, etc.

Substituents of the substituted phenyl group may include a fluorine atom, a chlorine atom, a bormine atom, an iodine atom, a straight or branched alkyl group having 1 to 5 carbon atoms, a straight or branched alkoxy group having 1 to 5 carbon atoms, a nitro group, a trifluoromethyl group, etc.

The straight or branched alkyl group having 1 to 20 carbon atoms may include a methyl group, an ethyl group, a propyl group, an isopropyl group, a butyl group, an isobutyl group, a sec-butyl group, a tert-butyl group, a pentyl group, an isopentyl group, a sec-pentyl group, a hexyl group, a 3-methylhexyl group, a 5-methylhexyl group, a heptyl group, a 5-methylheptyl group, 6-methylheptyl group, an octyl group, a 6-methyloctyl group, a 7-methyloctyl group, a 6-ethyloctyl group, a nonyl group, a 7-methylnonyl group, a 8-methylnonyl group, a 7-ethylnonyl group, a decyl group, a 8-methyldecyl group, a 9-methyldecyl group, a 8-ethyldecyl group, an undecyl group, a 9-methylundecyl group, a 10-methylundecyl group, a 9-ethylundecyl group, a dodecyl group, a 9-methyldodecyl group, a 10-methyldodecyl group, a tridecyl group, a tetradecyl group, a pentadecyl group, a hexadecyl group, a heptadecyl group, an octadecyl group, a nonadecyl group, an eicosyl group, etc.

The alkoxy group having 1 to 15 carbon atoms may include a methoxy group, an ethoxy group, a propoxy group, an isopropoxy group, a butoxy group, an isobutoxy group, a sec-butoxy group, a t-butoxy group, an amyloxy group, an isoamyloxy group, a hexyloxy group, a 3-methylhexyloxy group, a 2-ethylhexyloxy group, a heptyloxy group, an octyloxy group, a nonyloxy group, a decyloxy group, an undecyloxy group, a dodecyloxy group, a tridecyloxy group, a tetradecyloxy group, a pentadecyloxy group, etc.

The cycloalkylalkoxy group having 4 to 8 carbon atoms may include a cyclopropylmethoxy group, a cyclopropylethoxy group, a cyclobutylmethoxy group, a cyclobutylethoxy group, a cyclopentylmethoxy group, a cyclopentylethoxy group, a cyclohexylmethoxy group, a cyclohexylethoxy group, etc.

The lower alkoxyalkoxy group may include a methoxymethoxy group, an ethoxymethoxy group, a 1-ethoxyethoxy group, a 2-ethoxyethoxy group, a 2-propoxyethoxy group, a 2-isopropoxyethoxy group, a 2-butoxyethoxy group, 2-amyloxyethoxy group, a 3-methoxypropoxy group, a 4-methoxybutoxy group, a 5-methoxypentyloxy group, etc.

$R_1$ may preferably be a hydrogen atom, a chlorine atom or a methyl group.

$R_2$ may preferably be a chlorine atom or a bromine atom.

When $R_3$ is a lower alkyl group, preferred is a methyl group, an ethyl group or an isopropyl group, and when it is a cycloalkyl group having 3 to 6 carbon atoms, preferred is a cyclopropyl group.

When $R_4$ has no substituent, preferred is a pentyl group, a hexyl group, a heptyl group, an octyl group, a nonyl group, a 8-methylnonyl group or a decyl group, while it has a substituent(s), preferred is a 6-chlorohexyl group, a 6,6-difluorohexyl group, a 6-hydroxyhexyl group, a 7-hydroxyheptyl group, a 6-methoxyhexyl group, a 6-isopropoxyhexyl group, a 6-cyclopropylmethoxyhexyl group, a 7-methoxyheptyl group, a 6-(2-ethoxyethoxy)hexyl group, a 6-(1-ethoxyethoxy)hexyl group, a 7-(2-ethoxyethoxy)heptyl group, a 7-(1-ethoxyethoxy)heptyl group, a 5-(1,3-dioxoran-2-yl)pentyl group, a 6-acetyloxyhexyl group, a 6-(pyran-2-yloxy)-hexyl group, a 6-(N,N-dimethylcarbamoyloxy)hexyl group, a 6-(N,N-dimethylthiocarbamoyloxy)hexyl group, a 6-methanesulfonyloxyhexyl group, a 6-(imidazol-1-yl)hexyl group, etc.

As can be seen from the above formula (I), the compound of the present invention has an amino group so that acid addition salts can easily be formed, and such salts are also included in the present invention.

Acids to be formed salts may include, for example, inorganic acids such as hydrochloric acid, hydrobromic acid, nitric acid, sulfuric acid, phosphoric acid, etc.; carboxylic acids such as formic acid, oxalic acid, fumaric acid, adipic acid, stearic acid, oleic acid, aconitic acid, etc.; and organic acids such as methanesulfonic acid, benzenesulfonic acid, p-toluenesulfonic acid, etc.

In the above formula (I), when any of carbon atoms is an asymmetric carbon atom, its optical isomers and racemic compound or mixture thereof are all included in the present invention.

The compound (I) of the present invention can be easily prepared according to the process shown below, which are known per se in the art.

Preparation process A

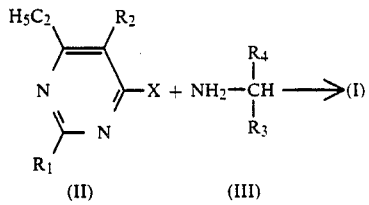

(II)    (III)

wherein $R_1$, $R_2$, $R_3$ and $R_4$ have the same meanings as defined above; and X represents an eliminatable group.

As described above, the reaction itself is known and therefore, there is no limitation concerning the eliminatable group X. The X may include, for example, a halogen atom such as a chlorine atom, a bromine atom or an iodine atom; an alkylthio group such as a methylthio group, an ethylthio group, a propylthio group, a butylthio group, etc.; an alkanesulfonyloxy group which may be substituted by a halogen atom such as a methanesulfonyloxy group, an ethanesulfonyloxy group, a trifluoromethanesulfonyloxy group, etc.; an arenesulfonyloxy group such as a benzenesulfonyloxy group, a p-toluenesulfonyloxy group, etc.; a mercapto group and a hydroxyl group, etc.

As clearly seen from the above reaction formula, in the present reaction, since a compound H—X is eliminated therefrom, the reaction is preferably carried out in the presence of a base in order to capture the compound and to proceed the reaction smoothly. The reaction is generally carried out in the presence of a solvent, but the reaction may be carried out by heating the compounds of the formula (II) and the formula (III) without any solvent.

The solvent is not particularly limited so long as it does not participate in the present reaction and may include, for example, chlorinated or not chlorinated aromatic, aliphatic or alicyclic hydrocarbons such as benzene, toluene, xylene, methylnaphthalene, petroleum ether, ligroin, hexane, chlorobenzene, dichlorobenzene, methylene chloride, chloroform, dichloroethane, trichloroethylene and cyclohexane; ethers such as diethyl ether, ethylene glycol dimethyl ether, tetrahydrofuran and dioxane; ketones such as acetone and methyl ethyl ketone; alcohols such as methanol, ethanol and ethylene glycol, or hydrates thereof; amides such as N,N-dimethylformamide (DMF), N,N-dimethylacetamide, etc.; and a mixture of the solvents described above; etc.

The base may include organic bases such as triethylamine, pyridine, N,N-diethylaniline, etc.; alkali metal alkoxide such as sodium methoxide, sodium ethoxide, etc.; inorganic bases such as sodium hydride, sodium amide, sodium hydroxide, potassium hydroxide, sodium carbonate, potassium carbonate, etc.

The reaction temperature is not particularly limited, but generally not less than the room temperature to the boiling point or less of the solvent to be used, and heating is preferably carried out to shorten the reaction time.

Preparation process B

In the above formula (I), when $R_4$ is a straight or branched alkyl group having 1 to 20 carbon atoms substituted by an alkoxy group having 1 to 15 carbon atoms, the compound can also be formed by the following known process.

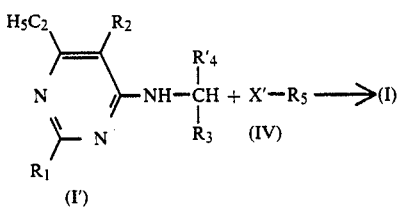

wherein $R_1$, $R_2$ and $R_3$ have the same meanings as defined above; $R'_4$ represents a straight or branched alkyl group having 1 to 20 carbon atoms substituted by a hydroxy group; $R_5$ represents an alkyl group having 1 to 15 carbon atoms;, and $X'$ represents an eliminatable group.

As described above, the reaction itself is known and therefore, there is no limitation concerning the eliminatable group X. The X may include, for example, a halogen atom such as a chlorine atom, a bromine atom or an iodine atom; an alkanesulfonyloxy group which may be substituted by a halogen atom such as a methanesulfonyloxy group, an ethanesulfonyloxy group, a trifluoromethanesulfonyloxy group, etc.; an arenesulfonyloxy group such as a benzenesulfonyloxy group, a p-toluenesulfonyloxy group, etc.

As clearly seen from the above reaction formula, in the present reaction, since a compound H—X is eliminated therefrom, the reaction is preferably carried out in the presence of a base in order to capture the compound and to proceed the reaction smoothly.

The reaction is generally carried out in the presence of a solvent, but the reaction may be carried out by heating the compounds of the formula (I') and the formula (IV) without any solvent.

The solvent is not particularly limited so long as it does not participate in the present reaction and may include, for example, chlorinated or not chlorinated aromatic, aliphatic or alicyclic hydrocarbons such as benzene, toluene, xylene, methylnaphthalene, petroleum ether, ligroin, hexane, chlorobenzene, dichlorobenzene, methylene chloride, chloroform, dichloroethane, trichloroethylene and cyclohexane; ethers such as diethyl ether, ethylene glycol dimethyl ether, tetrahydrofuran and dioxane; amides such as N,N-dimethylformamide (DMF), N,N-dimethylacetamide, etc.; and a mixture of the solvents described above; etc.

The base may include organic bases such as triethylamine, pyridine, N,N-diethylaniline, etc.; alkali metal alkoxide such as sodium methoxide, sodium ethoxide, etc.; inorganic bases such as sodium hydride, sodium amide, sodium hydroxide, potassium hydroxide, sodium carbonate, potassium carbonate, etc.

The reaction temperature is not particularly limited, but generally not less than the room temperature to the boiling point or less of the solvent to be used, and heating is preferably carried out to shorten the reaction time.

Preparation process C

In the above formula (I), when $R_4$ is a straight or branched alkyl group having 1 to 20 carbon atoms substituted by one halogen atom, the compounds may be prepared by the following reaction scheme.

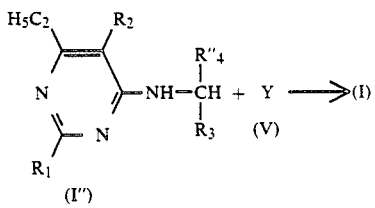

wherein $R_1$, $R_2$ and $R_3$ have the same meanings as defined above; $R''_4$ represents a straight or branched alkyl group having 1 to 20 carbon atoms substituted by one hydroxy group; and Y represents a halogenation agent.

As described above, the reaction itself is known and therefore, it is no limitation concerning the halogenation agent. The halogenation agent may include, for example, thionyl chloride, thionyl bromide, phosphorus trichloride, phosphorus tribromide, phosphorus oxychloride, phosphorus oxybromide, phosphorus pentachloride, phosphorus pentabromide, hydrogen chloride, hydrogen bromide, hydrogen fluoride, diethylaminosulfurtrifluoride (DAST), etc.

This reaction proceeds in the absence of a base but a base may be used in order to carry out the reaction smoothly.

The reaction is generally carried out in the presence of a solvent, but the reaction may be carried out by heating the compounds of the formula (I'') and the formula (V) without any solvent.

The solvent is not particularly limited so long as it does not participate in the present reaction and may include, for example, those as exemplified in the above preparation process A.

The base may preferably include organic bases such as triethylamine, pyridine, etc.

The reaction temperature is not particularly limited, but generally not less than the room temperature to the boiling point or less of the solvent to be used, and heating is preferably carried out to shorten the reaction time.

Preparation process D

In the above formula (I), when $R_4$ is a straight or branched alkyl group having 1 to 20 carbon atoms substituted by two fluorine atom, the compounds may be prepared by the following reaction scheme.

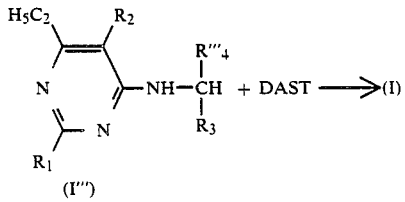

wherein $R_1$, $R_2$ and $R_3$ have the same meanings as defined above; $R'''_4$ represents a straight or branched alkyl group having 1 to 20 carbon atoms substituted by one formyl group; and DAST represents diethylaminosulfurtrifluoride.

The reaction is generally carried out in the presence of a solvent, but the reaction may be carried out by heating the compound of the formula (I''') and DAST without any solvent.

The solvent is not particularly limited so long as it does not participate in the present reaction and may include, for example, chlorinated or not chlorinated aromatic, aliphatic or alicyclic hydrocarbons such as benzene, toluene, xylene, methylnaphthalene, petroleum ether, ligroin, hexane, chlorobenzene, dichlorobenzene, methylene chloride, chloroform, dichloroethane, trichloroethylene and cyclohexane; ethers such as diethyl ether, ethylene glycol dimethyl ether, tetrahydrofuran and dioxane; and a mixture of the solvents described above; etc.

The reaction temperature is not particularly limited, but generally not less than the room temperature to the boiling point or less of the solvent to be used, and heating is preferably carried out to shorten the reaction time.

Preparation process E

In the above formula (I), when $R_4$ is a straight or branched alkyl group having 1 to 20 carbon atoms substituted by the substituent Q, the compounds may be prepared by the following reaction scheme.

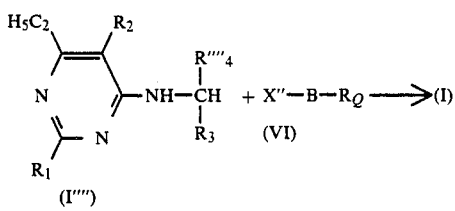

wherein $R_1$, $R_2$ and $R_3$ have the same meanings as defined above; $R''''_4$ represents a straight or branched alkyl group having 1 to 20 carbon atoms substituted by one AH group; where A has the same meaning as defined above; and X" represents an eliminatable group.

As described above, the reaction itself is known and therefore, there is no limitation concerning the eliminatable group X". The X" may include those as exemplified in the above preparation process A.

As clearly seen from the above reaction formula, in the present reaction, since a compound H—X" is eliminated therefrom, the reaction is preferably carried out in the presence of a base in order to capture the compound and to proceed the reaction smoothly.

The reaction is generally carried out in the presence of a solvent, but the reaction may be carried out by heating the compounds of the formula (I'''') and the formula (VI) without any solvent.

The solvent is not particularly limited so long as it does not participate in the present reaction and may include, for example, those as exemplified in the above preparation process A.

The base may preferably include those as exemplified in the preparation process A.

The reaction temperature is not particularly limited, but generally from 0° C. or higher to the boiling point or less of the solvent to be used.

Further, in order to heighten the reaction rate, a catalytic amount of 4-N,N-dialkylaminopyridines such as 4-N,N-dimethylaminopyridine, 4-pyrrolidinopyridine, etc. may preferably be added.

In the above preparation process, the compound of the formula (III) to be used as the starting material can be prepared, for example, by the following processes known per se.

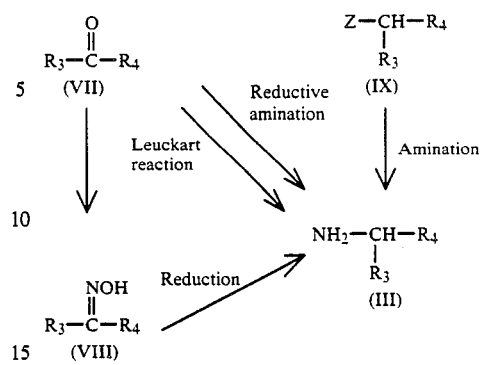

wherein $R_3$ and $R_4$ have the same meanings as defined above, and Z represents a halogen atom.

The desired product (I) obtained according to each of the processes as described above can be purified suitably by known means such as recrystallization, various chromatographies, etc.

An acid addition salt can be easily obtained by, for example, introducing an acid in a reaction mixture after completion of the reaction and then removing a solvent.

The compounds of the present invention exhibit excellent effects against Hemiptera such as planthoppers, leafhoppers, aphids, white flies, etc.; Leipdoptera such as cabbage armyworms, diamondback moth, leaf roller moths, pyralid moths, common white, etc.; Coleoptera such as weevils, leaf beetles, etc.; and other agricultural and horticultural injurious mites, for example, Acarina such as citrus red mite, two-spotted spider mite, etc. Also, they are very effective for prevention and extermination of hygienically injurious insects such as fly, mosquito, cockroach, etc., and also effective for other injurious insects against stored crops.

Further, the compounds of the present invention have also activities against root-knot nematode, pine wood nematode, bulb mite in the soil. Also, the compounds of the present invention are effective and active against diseases for agriculture and horticulture such as blast, powdery mildew, and otherwise downy mildew, gray mold, etc.

Thus, the uses and application fields of the compounds of the present invention are very wide, and therefore they can be provided for practical application in various dosage forms with high activities.

The insecticide, the acaricide and the fungicide of the present invention may comprise one or several kinds of the compounds of the formula (I) as active ingredients. Although the compound of the formula (I) may be used per se, it is generally formulated with common carriers, surfactants, dispersing agents or auxiliary agents, and prepared in a conventional manner into compositions such as powder, wettable powder, emulsion, fine granule, granule, aqueous or oily suspension, aerosol, etc. before use.

Suitable carriers may include, for example, solid carriers such as talc, bentonite, clay, kaolin, diatomaceous earth, white carbon, vermiculite, slaked lime, siliceous sand, ammonium sulfate, urea, etc.; liquid carriers, for example, hydrocarbons such as kerosene, mineral oil, etc.; aromatic hydrocarbons such as benzene, toluene, xylene, etc.; chlorinated hydrocarbons such as chloroform, carbon tetrachloride, etc.; ethers such as dioxane, tetrahydrofuran, etc.; ketones such as acetone, cyclohexanone, isophorone, etc.; esters such as ethyl acetate, ethylene glycol acetate, dibutyl maleate, etc.; alcohols such as methanol, n-hexanol, ethylene glycol, etc.; polar solvents such as dimethylformamide, dimethyl sulfoxide, etc.; or water. Also, as gaseous carrier, air, nitrogen, carbon dioxide, Freon, etc. can be used to effect mixed jetting.

Also, as the surfactant or the dispersing agent for improvement of attachment or absorption of the present agent onto animals and vegetables or for improvement of performances of dispersion, emulsification or spreading of the medicine, there may be employed, for example, alcohol sulfate esters, alkyl sulfonate salts, lignin sulfonate salts, polyoxyethylene glycol ethers, etc.

Further, for amelioration of the properties of the preparation, as the auxiliary agent, for example, carboxymethyl cellulose, polyethylene glycol, gum arabic, etc. may be employed.

The above carriers, surfactants, dispersing agents and auxiliary agents may be used either individually or in combination depending on the respective purposes.

The active ingredient concentration when the compound of the present invention is formed into a preparation may be generally 1 to 50% by weight for emulsion, generally 0.3 to 25% by weight for powder, generally 1 to 90% by weight for wettable powder, generally 0.5 to 5% by weight for granule, generally 0.5 to 5% by weight for oil and generally 0.1 to 5% by weight for aerosol.

These preparations can be diluted to appropriate concentrations, and provided for various uses depending on the respective purposes, such as by spraying onto stalks or leaves of vegetables, the surface of soil or paddy field, or alternatively by direct application.

EXAMPLES

The present invention is described below in more detail by referring to Examples, by which the present invention is not limited at all.

Example 1

Synthesis of dl-5-chloro-6-ethyl-4-(1-methyloctyl)aminopyrimidine (Compound No. 10)

In 40 ml of toluene was dissolved 1.3 g of 4,5-dichloro-6-ethylpyrimidine, and 3 g of triethylamine and 1.4 g of 1-methyloctylamine were added to the solution and the mixture was then refluxed for 10 hours under stirring. After completion of the reaction, the reaction mixture was extracted with ethyl acetate. The extract was washed with water and dried over anhydrous sodium sulfate and the solvent was removed under reduced pressure. The resulting oily product was isolated through a column chromatography (Wako gel C-200, trade name, eluent; toluent:ethyl acetate=8:1) to give 0.7 g of the title compound as colorless oily liquid. $n_D^{21.6}$ 1.5125.

Example 2

Synthesis of dl-5-chloro-6-ethyl-4-(1-ethylnonyl)aminopyrimidine (Compound No. 13)

In 40 ml of ethanol was dissolved 1.5 g of 4,5-dichloro-6-ethylpyrimidine, and 3 g of triethylamine and 1.3 g of 1-ethylnonylamine were added to the solution and the mixture was then refluxed for 10 hours under stirring. After completion of the reaction, the reaction mixture was extracted with ethyl acetate. The extract was washed with water and dried over anhydrous sodium sulfate and the solvent was removed under reduced pressure The resulting oily product was isolated through a column chromatography (Wako gel C-200, trade name, eluent; toluene ethyl acetate=8:1) to give 0.8 g of the title compound as colorless oily liquid. $n_D^{22.0}$ 1.5057.

Example 3

Synthesis of dl-5-chloro-6-ethyl-4-(1-ethyl-9-methyldecyl)aminopyrimidine (Compound No. 17)

In 40 ml of toluene was dissolved 1.4 g of 4,5-dichloro-6-ethylpyrimidine, and 5 g of pyridine and 1.1 g of 1-ethyl-9-methyldecylamine were added to the solution and the mixture was then refluxed for 10 hours under stirring. After completion of the reaction, the reaction mixture was extracted with ethyl acetate. The extract was washed with water and dried over anhydrous sodium sulfate and the solvent was removed under reduced pressure. The resulting oily product was isolated through a column chromatography (Wako gel C-200, trade name, eluent; toluene:ethyl acetate=8:1) to give 0.7 g of the title compound as colorless oily liquid. $n_D^{26.6}$ 1.5002.

Example 4

Synthesis of dl-5-chloro-6-ethyl-4-(1-cyclopropyldecyl)aminopyrimidine (Compound No. 21)

In 40 ml of toluene was dissolved 2.8 g of 4,5-dichloro-6-ethylpyrimidine, and 5 g of triethylamine and 3.3 g of 1-cyclopropyldecylamine were added to the solution and the mixture was then refluxed for 10 hours under stirring After completion of the reaction, the reaction mixture was extracted with ethyl acetate. The extract was washed with water and dried over anhydrous magnesium sulfate and the solvent was removed under reduced pressure The resulting oily product was isolated through a column chromatography (Wako gel C-200, trade name, eluent; toluene:ethyl acetate=8:1) to give 1.1 g of the title compound as colorless oily liquid. $n_D^{25.1}$ 1.5098.

Example 5

In the same manner as in Examples 1 to 4, the compounds Nos. 1 to 9, 11, 12, 14 to 16, 18 to 20 and 22 to 39 as shown in Table 1 were obtained.

Example 6

Synthesis of dl-5-chloro-6-ethyl-4-[1-ethyl-7-(1-ethoxyethoxy)heptyl]aminopyrimidine (Compound No. 62)

In 50 ml of toluene was dissolved 3.7 g of 4,5-dichloro-6-ethylpyrimidine, and 5 ml of triethylamine and 4.8 g of 1-ethyl-7-(1-ethoxyethoxy)heptylamine were added to the solution and the mixture was then refluxed for 10 hours under stirring. After completion of the reaction, the reaction mixture was filtered and excessive triethylamine and a solvent were removed under reduced pressure. The resulting oily product was isolated through a column chromatography (Wako gel C-200, trade name, eluent; toluene:ethyl acetate=3:1) to give 5.7 g of the title compound as colorless oily liquid. $n_D^{24.2}$ 1.4970.

Example 7

Synthesis of dl-5-chloro-6-ethyl-4-(1-ethyl-7-hydroxyheptyl)aminopyrimidine (Compound No. 47)

In 50 ml of ethanol was dissolved 4.7 g of dl-5-chloro-6-ethyl-4-[1-ethyl-7-(1-ethoxyethoxy)heptyl]aminopyrimidine, and 10 ml of 1N-HCl was added to the solution and the mixture was refluxed for one hour under stirring. After removing ethanol under reduced pressure, the residue was was made alkaline with a sodium hydroxide aqueous solution and was extracted with ethyl acetate. The organic layer was dried over anhydrous sodium sulfate and the solvent was removed under reduced pressure. The resulting oily product was isolated through a column chromatography (Wako gel C-200, trade name, eluent; toluene:ethyl acetate=2:1) to give 3.8 g of the title compound as pale yellow oily liquid. $n_D^{23.0}$ 1.5263.

Example 8

Synthesis of dl-5-chloro-6-ethyl-4-(1-ethyl-7-chloroheptyl)aminopyrimidine (Compound No. 40)

To a mixture of 0.9 g of dl-5-chloro-6-ethyl-4-(1-ethyl-7-hydroxyheptyl)aminopyrimidine and 0.28 g of pyridine was gradually added dropwise 0.42 g of thionyl chloride under cooling to −10° to −5° C. After dropwise addition, the mixture was heated at 60° to 70° C. for one hour and allowed to stand for cooling. The reaction mixture was neutralized with an aqueous sodium carbonate solution and extracted with ethyl acetate. The organic layer was dried over anhydrous sodium sulfate, and the solvent was removed under reduced pressure. The resulting oily product was isolated through a column chromatography (Wako gel C-200, trade name, eluent; toluene:ethyl acetate=10:1) to give 0.55 g of the title compound as pale yellow oily liquid. $n_D^{22.8}$ 1.5246.

Example 9

Synthesis of dl-5-chloro-6-ethyl-4-(1-ethyl-7-fluorononyl)aminopyrimidine (Compound No. 45)

In 20 ml of dichloromethane was dissolved 0.7 g of dl-5-chloro-6-etheyl-4-(1-ethyl-7-hydroxynonyl)aminopyrimidine, and 0.9 g of diethylaminosulfurtrifluoride (DAST) was added under stirring and the mixture was stirred at room temperature for 10 hours. After completion of the reaction, the mixture was poured into ice-cold water and extracted with dichloromethane. The organic layer was dried over anhydrous sodium sulfate, and the solvent was removed under reduced pressure. The resulting oily product was isolated through a column chromatography (Wako gel C-200, trade name, eluent; toluene:ethyl acetate=10:1) to give 0.4 g of the title compound as pale yellow oily liquid. $n_D^{25.0}$ 1.5027.

Example 10

Synthesis of dl-5-chloro-6-ethyl-4-(1-ethyl-7-methoxyheptyl)aminopyrimidine (Compound No. 54)

In 20 ml of anhydrous tetrahydrofuran was dissolved 0.56 g of dl-5-chloro-6-ethyl-4-(1-ethyl-7-hydroxyheptyl)aminopyrimidine, and 0.15 g of sodium hydride was added thereto. After stirring at room temperature for 30 minutes, 0.43 g of methyl iodide was added to the mixture, and the mixture was refluxed for 5 hours under stirring. After allowing to stand for cooling, an aqueous ammonium chloride solution was added to the reaction mixture and the reaction mixture was extracted with ethyl acetate. The organic layer was dried over anhydrous sodium sulfate, and the solvent was removed under reduced pressure. The resulting oily product was isolated through a column chromatography (Wako gel C-200, trade name, eluent; toluene:ethyl acetate=10:1) to give 0.19 g of the title compound as pale yellow oily liquid. $n_D^{23.0}$ 1.5094.

Example 11

Synthesis of dl-5-chloro-6-ethyl-4-[1-ethyl-6-(1,3-dioxoran-2-yl)hexyl]aminopyrimidine (Compound No. 66)

In 20 ml of toluene was dissolved 3.7 g of 4,5-dichloro-6-ethylpyrimidine, and 5 ml of triethylamine and 4.2 g of 1-ethyl-6-(1,3-dioxoran-2-yl)hexylamine were added to the solution and the mixture was refluxed for 12 hours under stirring. After completion of the reaction, the reaction mixture was filtered and excessive triethylamine and the solvent were removed under reduced pressure. The resulting oily product was isolated through a column chromatography (Wako gel C-200, trade name, eluent; toluene:ethyl acetate=3:1) to give 1.7 g of the title compound as pale yellow oily liquid. $n_D^{23.0}$ 1.5079.

Example 12

Synthesis of dl-5-chloro-6-ethyl-4-(1-ethyl-7,7-difluoroheptyl)aminopyrimidine (Compound No. 46)

In 10 ml of ethanol was dissolved 1.2 g of dl-5-chloro-6-ethyl-4-[1-ethyl-6-(1,3-dioxoran-2-yl)hexyl]aminopyrimidine, and 1 ml of 1N-HCl was added to the solution and the mixture was refluxed for 20 hours under stirring. Ethanol was removed under reduced pressure, and the residue was neutralized with an aqueous sodium carbonate solution and extracted with ethyl acetate. The organic layer was dried over anhydrous sodium sulfate and the solvent were removed under reduced pressure. The resulting oily product was isolated through a column chromatography (Wako gel C-200, trade name, eluent; toluene:ethyl acetate=5:1) to give 0.65 g of dl-5-chloro-6-ethyl-4-(1-ethyl-7-oxoheptyl)aminopyrimidine as colorless oily liquid. In 20 ml of dichloromethane was dissolved 0.65 g of this compound, and under stirring, 1 g of diethylaminosulfurtrifluoride (DAST) was added to the solution and the mixture was stirred at room temperature for 10 hours. After completion of the reaction, the reaction mixture was poured into ice-cold water and extracted with dichloromethane. After the organic layer was dried over anhydrous sodium sulfate, the solvent was removed under reduced pressure. The resulting oily product was isolated through a column chromatography (Wako gel C-200, trade name, eluent; toluene:ethyl acetate=10:1) to give 0.1 g of the title compound as pale yellow oily liquid. $n_D^{23.0}$ 1.4983.

Example 13

Synthesis of dl-5-chloro-6-ethyl-4-(6-acetoxyhexyl)aminopyrimidine (Compound No. 72)

In 10 ml of dichloromethane were dissolved 1.00 g of dl-5-chloro-6-ethyl-4-(6-hydroxyhexyl)aminopyrimidine and 0.40 g of acetyl chloride, and under stirring, 0.50 g of triethylamine was added to the solution and the mixture was stirred at room temperature for 30 minutes. After completion of the reaction, the reaction mixture was neutralized with an aqueous sodium carbonate solution and extracted with dichloromethane. After the organic layer was dried over anhydrous sodium sulfate, the solvent was removed under reduced pressure. The resulting oily product was isolated through a column chromatography (Wako gel C-200, trade name, eluent; toluene:ethyl acetate=4:1) to give 0.70 g of the title compound as pale yellow oily product. $n_D^{19.6}$ 1.5228.

Example 14

Synthesis of dl-5-chloro-6-ethyl-4-(6-ethoxycarbonyloxyhexyl)aminopyrimidine (Compound No. 89)

In 10 ml of dichloromethane were dissolved 0.70 g of dl-5-chloro-6-ethyl-4-(6-hydroxyhexyl)aminopyrimidine and 0.30 g of ethyl chloroformate, and under stirring, 0.40 g of triethylamine and a catalytic amount of 4-dimethylaminopyridine were added to the solution and the mixture was stirred at room temperature for 10 hours. After completion of the reaction, the reaction mixture was extracted with dichloromethane and washed with water. Then, the organic layer was dried over anhydrous sodium sulfate, the solvent was removed under reduced pressure. The resulting oily product was isolated through a column chromatography (Wako gel C-200, trade name, eluent; toluene:ethyl acetate=4:1) to give 0.30 g of the title compound as pale yellow oily product. $n_D^{18.7}$ 1.5138.

Example 15

Synthesis of dl-5-chloro-6-ethyl-4-[1-ethyl-7-(N,N-dimethylcarbamoyloxy)heptyl]aminopyrimidine (Compound No. 92)

In 10 ml of anhydrous tetrahydrofuran was dissolved 0.80 g of dl-5-chloro-6-ethyl-4-(1-ethyl-7-hydroxyheptyl)aminopyrimidine, and 0.13 g (60% by weight) of sodium hydride was added to the solution. After stirring at room temperature for 30 minutes, 0.35 g of N,N-dimethylcarbamoyl chloride was added thereto and the mixture was refluxed for 10 hours under stirring.

After allowed to stand for cooling, an aqueous ammonium chloride solution was added to the reaction mixture, and the mixture was extracted with ethyl acetate. After the organic layer was dried over anhydrous sodium sulfate, the solvent was removed under reduced pressure. The resulting oily product was isolated through a column chromatography (Wako gel C-200, trade name, eluent; toluene:ethyl acetate=3:1) to give 0.25 g of the title compound as pale yellow oily product. $n_D^{19.2}$ 1.5164.

Example 16

Synthesis of dl-5-chloro-6-ethyl-4-[1-ethyl-7-(imidazol-1-ylcarbonyloxy)heptyl]aminopyrimidine (Compound No. 98)

In 20 ml of toluene was dissolved 1.00 g of dl-5-chloro-6-ethyl-4-[1-ethyl-7-(chlorocarbonyloxy)heptyl]aminopyrimidine, and 0.50 g of triethylamine and 0.22 g of imidazole were added to the solution and the mixture was stirred at room temperature for one hour. After completion of the reaction, the reaction mixture was filtered, and excessive triethylamine and the solvent was removed under reduced pressure. The resulting oily product was isolated through a column chromatography (Wako gel C-200, trade name, eluent; toluene:ethyl acetate=3:1) to give 0.80 g of the title compound as pale yellow oily product. $n_D^{21.9}$ 1.5332.

Example 17

Synthesis of dl-5-chloro-6-ethyl-4-[1-ethyl-7-(methanesulfonyloxy)heptyl]aminopyrimidine (Compound No. 100)

In 15 ml of dichloromethane was dissolved 1.00 g of dl-5-chloro-6-ethyl-4-(1-ethyl-7-hydroxypentyl)aminopyrimidine, and under ice cooling, 0.50 g of triethylamine was added to the solution and the mixture was stirred for one hour. After completion of the reaction, an aqueous sodium hydrogen carbonate solution was added to the reaction mixture and the mixture was extracted with dichloromethane. After the organic layer was dried over anhydrous sodium sulfate, the solvent was removed under reduced pressure. The resulting oily product was isolated through a column chromatography (Wako gel C-200, trade name, eluent; toluene:ethyl acetate=4:1) to give 0.70 g of the title compound as pale yellow oily product. $n_D^{18.4}$ 1.5209.

Example 18

Synthesis of dl-5-chloro-6-ethyl-4-(1-ethyl-7-acetylaminoheptyl)aminopyrimidine (Compound No. 102)

In 10 ml of chloroform were dissolved 0.55 g of dl-5-chloro-6-ethyl-4-(1-ethyl-7-aminoheptyl)aminopyrimidine and 0.25 g of triethylamine, and under ice cooling, 0.18 g of acetyl chloride was added to the solution and the mixture was stirred for one hour. After completion of the reaction, the reaction mixture was extracted with chloroform. After the organic layer was dried over anhydrous sodium sulfate, the solvent was removed under reduced pressure. The resulting oily product was isolated through a column chromatography (Wako gel C-200, trade name, eluent; ethyl acetate) to give 0.20 g of the title compound as pale yellow oily product. $n_D^{22.4}$ 1.5296.

Example 19

Synthesis of dl-5-chloro-6-ethyl-4-[1-ethyl-7-(imidazol-1-yl)heptyl]aminopyrimidine (Compound No. 105)

In 10 ml of dimethylformamide was dissolved 0.32 g of imidazole, and 0.30 g (60% by weight) of sodium hydride was added to the solution. After stirring at room temperature for 10 minutes, 1.00 g of dl-5-chloro-6-ethyl-4-(1-ethyl-7-chloroheptyl)aminopyrimidine was added to the mixture and the mixture was heated to 100° to 110° C. under stirring.

After allowed to stand for cooling, an aqueous ammonium chloride solution was added to the reaction mixture, and the mixture was extracted with ethyl acetate. After the organic layer was dried over anhydrous sodium sulfate, the solvent was removed under reduced pressure. The resulting oily product was isolated through a column chromatography (Wako gel C-200, trade name, eluent; toluene:ethyl acetate=3:1) to give 0.55 g of the title compound as pale yellow oily product. $n_D^{25.6}$ 1.5342.

Example 20

In the same manner as in Examples 6 to 19, the compounds Nos. 41 to 44, 48 to 53, 55 to 61, 63 to 65, 67 to 71, 73 to 88, 90, 91, 93 to 97, 99, 101, 103, 104 and 106 to 108 as shown in Table 1 were obtained.

TABLE 1

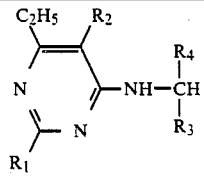

| Comp. No. | $R_1$ | $R_2$ | $R_3$ | $R_4$ | Physical property |
|---|---|---|---|---|---|
| 1 | H | Cl | $CH_3$ | $-CH_2CH(CH_3)_2$ | $n_D^{20.2}$ 1.5192 |
| 2 | " | " | " | $-(CH_2)_3CH_3$ | $n_D^{20.0}$ 1.5179 |
| 3 | " | " | $C_2H_5$ | " | $n_D^{21.8}$ 1.5180 |
| 4 | " | " | $CH_3$ | $-(CH_2)_4CH_3$ | $n_D^{21.4}$ 1.5154 |
| 5 | " | " | $C_2H_5$ | " | $n_D^{21.7}$ 1.5145 |
| 6 | " | " | $CH_3$ | $-(CH_2)_5CH_3$ | $n_D^{20.0}$ 1.5078 |
| 7 | " | " | $C_2H_5$ | " | $n_D^{21.8}$ 1.5115 |
| 8 | " | " | $C_3H_7$ | " | $n_D^{21.4}$ 1.5078 |
| 9 | " | " | ▷ | " | $n_D^{24.2}$ 1.5154 |
| 10 | " | " | $CH_3$ | $-(CH_2)_6CH_3$ | $n_D^{21.6}$ 1.5125 |
| 11 | H | Cl | $C_2H_5$ | $-(CH_2)_6CH_3$ | $n_D^{21.4}$ 1.5092 |
| 12 | " | " | ▷ | " | $n_D^{25.6}$ 1.5082 |
| 13 | " | " | $C_2H_5$ | $-(CH_2)_7CH_3$ | $n_D^{22.0}$ 1.5057 |
| 14 | " | " | $C_3H_7$ | " | $n_D^{23.5}$ 1.5054 |
| 15 | " | " | i-$C_3H_7$ | " | $n_D^{23.4}$ 1.4964 |
| 16 | " | " | ▷ | " | $n_D^{22.4}$ 1.5102 |
| 17 | " | " | $C_2H_5$ | $-(CH_2)_7CH(CH_3)_2$ | $n_D^{26.6}$ 1.5002 |
| 18 | " | " | H | $-(CH_2)_8CH_3$ | $n_D^{22.2}$ 1.5127 |
| 19 | " | " | $CH_3$ | " | $n_D^{22.2}$ 1.5014 |
| 20 | " | " | $C_2H_5$ | " | $n_D^{25.0}$ 1.5004 |
| 21 | " | " | ▷ | $-(CH_2)_8CH_3$ | $n_D^{25.1}$ 1.5098 |
| 22 | " | " | $C_2H_5$ | $-(CH_2)_9CH_3$ | $n_D^{23.7}$ 1.5025 |
| 23 | " | " | " | $-(CH_2)_{11}CH_3$ | $n_D^{22.6}$ 1.4928 |
| 24 | " | " | " | $-(CH_2)_{13}CH_3$ | $n_D^{22.8}$ 1.4769 |
| 25 | H | Cl | H | $-(CH_2)_{16}CH_3$ | m.p. 48~50° C. |
| 26 | H | Cl | $CH_3$ | $-(CH_2)_7CH_3$ | $n_D^{27.4}$ 1.5014 |
| 27 | " | Br | " | $-(CH_2)_8CH_3$ | $n_D^{24.8}$ 1.5146 |
| 28 | $CH_3$ | Cl | " | " | $n_D^{23.2}$ 1.5036 |
| 29 | H | " | " | $-(CH_2)_7CH(CH_3)C_3H_7$ | $n_D^{23.3}$ 1.5116 |
| 30 | $C_2H_5$ | " | " | $-(CH_2)_8CH_3$ | $n_D^{25.7}$ 1.4988 |
| 31 | $C_3H_7$ | " | " | " | $n_D^{25.7}$ 1.4965 |
| 32 | i-$C_3H_7$ | " | " | " | $n_D^{25.8}$ 1.4933 |
| 33 | ▷ | " | " | " | $n_D^{25.8}$ 1.5107 |
| 34 | Ph | " | " | " | $n_D^{22.6}$ 1.5509 |
| 35 | $CH_2Cl$ | " | " | " | $n_D^{20.7}$ 1.5118 |
| 36 | Cl | " | " | " | $n_D^{20.6}$ 1.5188 |

TABLE 1-continued

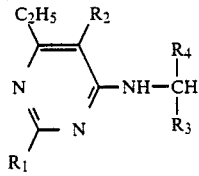

| Comp. No. | $R_1$ | $R_2$ | $R_3$ | $R_4$ | Physical property |
|---|---|---|---|---|---|
| 37 | $C_2H_5$ | " | H | " | $n_D^{17.9}$ 1.5051 |
| 38 | $C_3H_7$ | " | " | " | $n_D^{17.8}$ 1.5043 |
| 39 | i-$C_3H_7$ | Cl | H | $\text{-}(CH_2)_3CH_3$ | $n_D^{17.9}$ 1.5012 |
| 40 | H | " | $C_2H_5$ | $\text{-}(CH_2)_5CH_2Cl$ | $n_D^{22.8}$ 1.5246 |
| 41 | " | " | " | $\text{-}(CH_2)_7CH_2Cl$ | $n_D^{26.0}$ 1.5164 |
| 42 | " | " | " | $\text{-}(CH_2)_5CHClCH_2CH_2CH_3$ | $n_D^{20.3}$ 1.5504 |
| 43 | " | " | H | $\text{-}(CH_2)_4CH_2F$ | $n_D^{24.8}$ 1.5160 |
| 44 | " | " | $C_2H_5$ | $\text{-}(CH_2)_5CH_2F$ | Note 1 |
| 45 | " | " | " | $\text{-}(CH_2)_7CH_2F$ | $n_D^{25.0}$ 1.5027 |
| 46 | " | " | " | $\text{-}(CH_2)_5CHF_2$ | $n_D^{23.0}$ 1.4983 |
| 47 | " | " | " | $\text{-}(CH_2)_5CH_2OH$ | $n_D^{23.0}$ 1.5263 |
| 48 | " | " | H | $-CH_2CH_2O\text{-}(CH_2)_5CH_3$ | $n_D^{20.4}$ 1.5146 |
| 49 | " | " | " | $-CH_2CH_2O\text{-}(CH_2)_{11}CH_3$ | $n_D^{20.2}$ 1.4992 |
| 50 | " | " | " | $-CH_2CH_2OCH_2CH(CH_3)_2$ | $n_D^{20.2}$ 1.5121 |
| 51 | " | " | " | $\text{-}(CH_2)_2O-CH_2-CH(C_2H_5)\text{-}(CH_2)_3CH_3$ | $n_D^{20.2}$ 1.5067 |
| 52 | H | Cl | H | $\text{-}(CH_2)_3OCH_2CH_2CH_3$ | $n_D^{25.0}$ 1.5124 |
| 53 | " | " | " | $\text{-}(CH_2)_4OCH_2CH_3$ | $n_D^{28.2}$ 1.5158 |
| 54 | " | " | $C_2H_5$ | $\text{-}(CH_2)_5CH_2OCH_3$ | $n_D^{23.0}$ 1.5094 |
| 55 | " | " | " | $\text{-}(CH_2)_5CH_2OCH(CH_3)_2$ | $n_D^{22.8}$ 1.4990 |
| 56 | " | " | " | $\text{-}(CH_2)_5CH_2OCH_2\text{-cyclopropyl}$ | $n_D^{20.7}$ 1.5127 |
| 57 | " | " | " | $\text{-}(CH_2)_7CH_2OCH_3$ | $n_D^{25.0}$ 1.4954 |
| 58 | " | " | " | $\text{-}(CH_2)_7CH_2O\text{-}(CH_2)_4CH_3$ | $n_D^{25.4}$ 1.4958 |
| 59 | " | " | " | $\text{-}(CH_2)_5CH(OCH_3)CH_2CH_2CH_3$ | $n_D^{22.8}$ 1.5040 |
| 60 | " | " | " | $\text{-}(CH_2)_5CH_2OCH_2CH_2OCH_2CH_3$ | $n_D^{21.8}$ 1.5010 |
| 61 | " | " | " | $\text{-}(CH_2)_7CH_2OCH_2CH_2OCH_2CH_3$ | $n_D^{22.8}$ 1.4913 |
| 62 | " | " | " | $\text{-}(CH_2)_5CH_2OCH(CH_3)OCH_2CH_3$ | $n_D^{24.2}$ 1.4970 |
| 63 | " | " | " | $\text{-}(CH_2)_7CH_2OCH(CH_3)OCH_2CH_3$ | $n_D^{21.9}$ 1.4962 |
| 64 | " | " | " | $\text{-}(CH_2)_5CH(CH_2CH_2CH_3)OCH(CH_3)OCH_2CH_3$ | $n_D^{21.2}$ 1.4781 |
| 65 | H | Cl | H | $\text{-}(CH_2)_5CH$ (1,3-dioxolane) | $n_D^{23.0}$ 1.5204 |
| 66 | " | " | $C_2H_5$ | $\text{-}(CH_2)_5CH$ (1,3-dioxolane) | $n_D^{23.0}$ 1.5079 |
| 67 | " | " | H | $\text{-}(CH_2)_4CH_2OH$ | $n_D^{19.4}$ 1.5473 |
| 68 | " | " | " | $\text{-}(CH_2)_5CH_2OH$ | $n_D^{21.6}$ 1.5409 |
| 69 | " | " | $C_2H_5$ | $\text{-}(CH_2)_7CH_2OH$ | $n_D^{16.0}$ 1.5294 |
| 70 | " | " | H | $\text{-}(CH_2)_4CH_2OCH(CH_3)OCH_2CH_3$ | $n_D^{15.8}$ 1.5110 |
| 71 | " | " | " | $\text{-}(CH_2)_5CH_2OCH(CH_3)OCH_2CH_3$ | $n_D^{15.8}$ 1.5085 |
| 72 | " | " | " | $\text{-}(CH_2)_4CH_2OC(=O)CH_3$ | $n_D^{19.6}$ 1.5228 |
| 73 | " | " | " | $\text{-}(CH_2)_5CH_2OC(=O)CH_3$ | $n_D^{19.9}$ 1.5714 |
| 74 | " | " | " | $\text{-}(CH_2)_4CH_2OC(=O)CH_2CH_2CH_3$ | $n_D^{21.6}$ 1.5095 |

TABLE 1-continued

Structure:
$C_2H_5$ and $R_2$ on vinyl group attached to pyrimidine ring with $R_1$, connected via NH—CH($R_3$)($R_4$)

| Comp. No. | $R_1$ | $R_2$ | $R_3$ | $R_4$ | Physical property |
|---|---|---|---|---|---|
| 75 | " | " | " | $-(CH_2)_4CH_2OC(=O)CH_2Cl$ | $n_D^{21.6}$ 1.5316 |
| 76 | H | Cl | H | $-(CH_2)_5CH_2OC(=O)$-phenyl | $n_D^{19.8}$ 1.5462 |
| 77 | " | " | $C_2H_5$ | $-(CH_2)_5CH_2OC(=O)CH_3$ | $n_D^{23.0}$ 1.5091 |
| 78 | " | " | " | $-(CH_2)_5CH_2OC(=O)CH_2CH_2CH_2CH_3$ | $n_D^{18.6}$ 1.5216 |
| 79 | " | " | " | $-(CH_2)_7CH_2OC(=O)CH_3$ | $n_D^{22.2}$ 1.5032 |
| 80 | " | " | " | $-(CH_2)_7CH_2OC(=O)CH_2CH_2CH_2CH_3$ | $n_D^{23.6}$ 1.4971 |
| 81 | " | " | " | $-(CH_2)_5CH_2OC(=O)C(CH_3)_3$ | $n_D^{20.6}$ 1.5001 |
| 82 | " | " | " | $-(CH_2)_5CH_2OC(=O)CH_2Cl$ | $n_D^{18.4}$ 1.5042 |
| 83 | " | " | " | $-(CH_2)_5CH_2OC(=O)$-phenyl | $n_D^{18.0}$ 1.5438 |
| 84 | " | " | " | $-(CH_2)_5CH_2OC(=O)$-cyclopropyl | $n_D^{20.0}$ 1.5173 |
| 85 | H | Cl | $C_2H_5$ | $-(CH_2)_5CH_2OCH_2$-C$_6$H$_4$-$C(CH_3)_3$ | $n_D^{21.0}$ 1.5320 |
| 86 | " | " | " | $-(CH_2)_5CH_2O$-(tetrahydropyran-2-yl) | $n_D^{24.0}$ 1.5098 |
| 87 | " | " | " | $-CH_2OCH_2CH_2OCH_2CH_2OCH_2CH_3$ | $n_D^{27.2}$ 1.4996 |
| 88 | " | " | " | $-CH_2OCH_2CH_2OCH_2CH_2O(CH_2)_3CH_3$ | $n_D^{26.8}$ 1.4954 |
| 89 | " | " | H | $-(CH_2)_4CH_2OC(=O)CH_2CH_3$ | $n_D^{18.7}$ 1.5138 |
| 90 | " | " | $C_2H_5$ | $-(CH_2)_5CH_2OC(=O)O$-phenyl | $n_D^{21.8}$ 1.5322 |

TABLE 1-continued structure: pyrimidine with $C_2H_5$ and $R_2$ substituents, $R_1$ on ring, NH-CH($R_3$)($R_4$) side chain

| Comp. No. | $R_1$ | $R_2$ | $R_3$ | $R_4$ | Physical property |
|---|---|---|---|---|---|
| 91 | " | " | " | $-(CH_2)_5CH_2OCNHCH_3$ (C=O) | m.p. 90~92° C. |
| 92 | " | " | " | $-(CH_2)_5CH_2OCN(CH_3)_2$ (C=O) | $n_D^{19.2}$ 1.5164 |
| 93 | " | " | " | $-(CH_2)_5CH_2OCN(C_2H_5)_2$ (C=O) | $n_D^{23.0}$ 1.5042 |
| 94 | " | " | " | $-(CH_2)_5CH_2OCNH$-(3-Cl-phenyl) (C=O) | m.p. 78.5~81° C. |
| 95 | H | Cl | $C_2H_5$ | $-(CH_2)_5CH_2OCN$(2,6-dimethylmorpholino) (C=O) (trans) | $n_D^{22.9}$ 1.5110 |
| 96 | " | " | " | $-(CH_2)_5CH_2OCN$(2,6-dimethylmorpholino) (C=O) (cis) | $n_D^{21.6}$ 1.5126 |
| 97 | " | " | " | $-(CH_2)_5CH_2OCN$(4-methylpiperazinyl) (C=O) | $n_D^{22.2}$ 1.5200 |
| 98 | " | " | " | $-(CH_2)_5CH_2OC$-N(imidazolyl) (C=O) | $n_D^{21.9}$ 1.5332 |
| 99 | " | " | " | $-(CH_2)_5CH_2OCN(CH_3)_2$ (C=S) | $n_D^{23.4}$ 1.5448 |
| 100 | " | " | " | $-(CH_2)_5CH_2OSCH_3$ (S with two =O) | $n_D^{18.4}$ 1.5209 |
| 101 | " | " | " | $-(CH_2)_5CH_2OS$(=O)$_2$-(4-methylphenyl) | $n_D^{22.0}$ 1.5401 |
| 102 | " | " | " | $-(CH_2)_5CH_2NHCOCH_3$ | $n_D^{22.4}$ 1.5296 |
| 103 | H | Cl | $C_2H_5$ | $-(CH_2)_5CH_2NHCON(CH_3)_2$ | $n_D^{22.9}$ 1.5173 |
| 104 | " | " | " | $-(CH_2)_5CH_2COOCH_3$ | $n_D^{19.0}$ 1.5133 |

TABLE 1-continued $$\begin{array}{c} C_2H_5 \quad R_2 \\ \diagdown \quad / \\ N \quad \diagup NH-CH(R_4)(R_3) \\ \diagup \quad \diagdown N \\ R_1 \end{array}$$

| Comp. No. | $R_1$ | $R_2$ | $R_3$ | $R_4$ | Physical property |
|---|---|---|---|---|---|
| 105 | " | " | " | $-(CH_2)_5CH_2-N\diagup\!\!\diagdown\!\!N=\!\!\diagdown$ | $n_D^{25.6}$ 1.5342 |
| 106 | " | " | " | $-(CH_2)_2-\!\!\diagup\!\!\diagdown\!\!H$ (cyclohexyl) | $n_D^{24.8}$ 1.5252 |
| 107 | F | " | " | $-(CH_2)_8CH_3$ | $n_D^{21.8}$ 1.5006 |
| 108 | H | " | " | $-(CH_2)_6CH_3$.hydrochloride | — |

Note 1
$^1$H-NMR(CDCl$_3$) δ ppm 0.95(3H, t, J=8Hz), 1.22~1.82(15H, m), 2.77(2H, q, J=8Hz), 4.11~4.23(1H, m), 4.43(2H, dt, J=50Hz, 8Hz), 5.03~5.15(1H, br), 8.38(1H, s).

Example 21

5 parts by weight of the compound of the Compound No. 7, 35 parts by weight of bentonite, 57 parts by weight of talc, 1 part by weight of Neopelex Powder (trade name, produced by Kao-Atlas Co.) and 2 parts by weight of sodium lignosulfate were homogeneously mixed, then kneaded with addition of a small amount of water, followed by granulation and drying to obtain granules.

Example 22

10 parts by weight of the compound of the Compound No. 54, 70 parts by weight of kaolin, 18 parts by weight of white carbon, 1.5 parts by weight of Neopelex Powder (trade name, produced by Kao-Atlas Co.) and 0.5 part by weight of Demol (trade name, produced by Kao-Atlas Co.) were homogeneously mixed, followed by pulverization, to obtain wettable powder.

Example 23

To 20 parts by weight of the compound of the Compound No. 17 and 70 parts by weight of xylene were added 10 parts by weight of Toxanon (trade name, produced by Sanyo Kasei Kogyo, Co.), and homogeneously mixed and dissolved to obtain an emulsion.

Example 24

5 parts by weight of the compound of the Compound No. 19, 50 parts by weight of talc and 45 parts by weight of kaolin were homogeneously mixed to obtain powder.

Example 25

Activity test against common cutworm

The compounds shown in Table 1 were formed into preparations similarly as in Example 21, diluted with water containing a surfactant (0.03%) to 300 ppm. On the other hand, in plastic cups of 10 cm in diameter, leaves of soybean were laid, and 10 second-instar larvae of common cutworm were provided for test on the leaves. The medicinal solution prepared was sprayed each in 5 ml in a spraying tower. Then, the leaf was left to stand in a thermostat chamber at 25° C., and the numbers of alive and dead insects after 2 days were examined to determine the insecticide ratio. The results are shown in Table 2.

In the evaluation of effects, those with insecticide ratio of 100% are shown as 5, 99 to 80% as 4, 59 to 40% as 3, 39 to 20% as 2 and 19 to 0% as 1 and these also apply to the following tests.

As a control, a compound represented by the following formula (hereinafter called as "Compound A") which had been described in Japanese Provisional Patent Publication No. 170077/1984 was used.

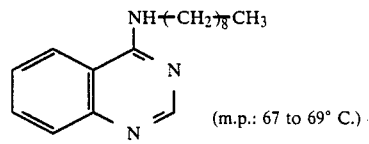

(m.p.: 67 to 69° C.)

TABLE 2

| Compound No. | Effect | Compound No. | Effect |
|---|---|---|---|
| 9 | 5 | 21 | 5 |
| 10 | 5 | 22 | 4 |
| 11 | 5 | 26 | 5 |
| 12 | 5 | 27 | 5 |
| 13 | 5 | 28 | 5 |
| 16 | 5 | 29 | 5 |
| 17 | 4 | 36 | 4 |
| 19 | 5 | | |
| 20 | 5 | Compound A | 1 |

Example 26

Activity test against diamondback moth (organic phosphorus agent resistance)

In plastic cups of 10 cm in diameter, cabbage leaf strips (5 cm×5 cm) were placed, while the medicinal solutions prepared by forming the compounds shown in Table 1 into preparations similarly as in Example 22 and diluting with water containing a surfactant (0.03%) to 300 ppm were sprayed each in 5 ml in a spraying tower. After drying on air, 10 third-instar larvae of diamondback moth were provided for test, left to stand in a thermostat chamber at 25° C. After 2 days, the numbers of alive and dead insects were examined to determine the insecticide ratio. The results are shown in Table 3.

TABLE 3

| Compound No. | Effect | Compound No. | Effect | Compound No. | Effect |
|---|---|---|---|---|---|
| 3 | 4 | 24 | 4 | 60 | 5 |
| 4 | 4 | 26 | 5 | 61 | 5 |
| 5 | 5 | 27 | 5 | 62 | 4 |
| 6 | 5 | 28 | 5 | 63 | 5 |
| 7 | 5 | 29 | 5 | 65 | 5 |
| 9 | 5 | 36 | 4 | 66 | 5 |
| 10 | 5 | 40 | 5 | 69 | 4 |
| 11 | 5 | 41 | 4 | 71 | 4 |
| 12 | 5 | 42 | 4 | 74 | 4 |
| 13 | 5 | 43 | 5 | 79 | 4 |
| 14 | 4 | 44 | 5 | 80 | 5 |
| 15 | 4 | 46 | 5 | 85 | 4 |
| 16 | 5 | 52 | 5 | 92 | 5 |
| 17 | 5 | 53 | 4 | 93 | 4 |
| 18 | 5 | 54 | 5 | 99 | 4 |
| 19 | 5 | 55 | 5 | 100 | 5 |
| 20 | 5 | 56 | 4 | 105 | 5 |
| 21 | 5 | 57 | 5 | 107 | 5 |
| 22 | 5 | 58 | 5 | 108 | 5 |
| 23 | 4 | 59 | 4 | Compound A | 2 |

Example 27

Activity test against brown rice planthopper

In the medicinal solutions prepared by forming the compounds shown in Table 1 into preparations similarly as in Example 22 and diluting with water containing a surfactant (0.03%) to 300 ppm, rice seedlings were dipped for 30 seconds and after drying on air inserted into a glass cylinder. Ten third-instar larvae of brown rice planthopper were freed, and left to stand in a thermostat chamber at 25° C. with attachment of a porous stopper. After 2 days, the numbers of alive and dead insects were examined to determine the insecticide ratio. The results are shown in Table 4.

TABLE 4

| Compound No. | Effect | Compound No. | Effect |
|---|---|---|---|
| 1 | 4 | 28 | 5 |
| 2 | 5 | 29 | 5 |
| 3 | 5 | 36 | 5 |
| 4 | 4 | 40 | 4 |
| 5 | 5 | 44 | 5 |
| 6 | 5 | 46 | 5 |
| 7 | 5 | 53 | 4 |
| 9 | 5 | 54 | 4 |
| 10 | 5 | 55 | 5 |
| 11 | 5 | 56 | 4 |
| 12 | 5 | 57 | 4 |
| 13 | 5 | 58 | 4 |
| 14 | 5 | 59 | 4 |
| 15 | 5 | 60 | 4 |
| 16 | 5 | 61 | 5 |
| 17 | 5 | 65 | 5 |
| 18 | 4 | 66 | 5 |
| 19 | 5 | 70 | 5 |
| 20 | 5 | 71 | 5 |
| 21 | 5 | 92 | 4 |
| 22 | 5 | 105 | 5 |
| 23 | 5 | 107 | 5 |
| 26 | 5 | 108 | 5 |
| 27 | 5 | Compound A | 1 |

Example 28

Activity test against green rice leafhopper (organic phosphorus agent resistance)

In the medicinal solutions prepared by forming the compounds shown in Table 1 into preparations similarly as in Example 22 and diluting with water containing a surfactant (0.03%) to 300 ppm, rice seedlings were dipped for 30 seconds and after drying on air inserted into a glass cylinder. Ten four-instar larvae of green rice leafhopper were freed, and left to stand in a thermostat chamber at 25° C. with attachment of a porous stopper. After 2 days, the numbers of alive and dead insects were examined to determine the insecticide ratio. The results are shown in Table 5.

TABLE 5

| Compound No. | Effect | Compound No. | Effect |
|---|---|---|---|
| 2 | 5 | 41 | 5 |
| 3 | 5 | 42 | 4 |
| 4 | 5 | 43 | 4 |
| 5 | 5 | 44 | 5 |
| 6 | 5 | 45 | 5 |
| 7 | 5 | 46 | 5 |
| 9 | 5 | 52 | 4 |
| 10 | 5 | 54 | 5 |
| 11 | 5 | 55 | 5 |
| 12 | 5 | 56 | 5 |
| 13 | 5 | 57 | 5 |
| 14 | 5 | 58 | 5 |
| 15 | 5 | 59 | 5 |
| 16 | 5 | 60 | 5 |
| 17 | 5 | 61 | 5 |
| 19 | 5 | 62 | 5 |
| 20 | 5 | 63 | 4 |
| 21 | 5 | 65 | 4 |
| 22 | 5 | 66 | 5 |
| 23 | 5 | 86 | 5 |
| 26 | 5 | 99 | 5 |
| 27 | 5 | 102 | 5 |
| 28 | 5 | 105 | 4 |
| 29 | 5 | 107 | 5 |
| 36 | 5 | 108 | 5 |
| 40 | 5 | Compound A | 1 |

Example 29

Activity test against adult female two-spotted spider mite (organic phosphorous agent resistance)

On filter papers soaked with water, kidney bean leaf strips of 20 mm in diameter were placed and 10 adult female two-spotted spider mites were inoculated. The leaf strips were dipped for 15 seconds in medical solutions prepared by forming the compounds shown in Table 1 into preparation similarly as in Example 22 and diluting with water containing a surfactant (0.03%) to 300 ppm. After drying on air, the leaf strips were left to stand in a thermostat chamber at 25° C. After 3 days, the numbers of alive and dead insects were examined to determine the acaricide ratio. The results are shown in Table 6.

TABLE 6

| Compound No. | Effect | Compound No. | Effect | Compound No. | Effect |
|---|---|---|---|---|---|
| 1 | 4 | 36 | 5 | 66 | 5 |
| 2 | 5 | 40 | 5 | 70 | 5 |
| 4 | 4 | 41 | 5 | 71 | 5 |
| 5 | 4 | 42 | 5 | 72 | 5 |
| 6 | 5 | 43 | 5 | 73 | 4 |
| 7 | 4 | 44 | 5 | 75 | 5 |
| 9 | 5 | 45 | 5 | 76 | 4 |

TABLE 6-continued

| Compound No. | Effect | Compound No. | Effect | Compound No. | Effect |
|---|---|---|---|---|---|
| 10 | 4 | 46 | 5 | 79 | 5 |
| 11 | 5 | 50 | 4 | 84 | 4 |
| 12 | 5 | 51 | 5 | 86 | 5 |
| 13 | 5 | 52 | 5 | 91 | 4 |
| 15 | 5 | 53 | 5 | 92 | 5 |
| 16 | 5 | 54 | 5 | 93 | 5 |
| 18 | 5 | 55 | 5 | 95 | 4 |
| 19 | 5 | 56 | 5 | 96 | 5 |
| 20 | 5 | 57 | 5 | 97 | 4 |
| 21 | 5 | 58 | 5 | 99 | 5 |
| 22 | 5 | 59 | 5 | 101 | 5 |
| 23 | 5 | 60 | 5 | 105 | 5 |
| 26 | 5 | 61 | 5 | 106 | 4 |
| 27 | 5 | 62 | 5 | 107 | 5 |
| 28 | 5 | 63 | 5 | Compound A | 5 |
| 29 | 5 | 65 | 5 | | |

Example 30

Activity test against two-spotted spider mite egg (organic phosphorus agent resistance)

On filter papers soaked with water, kidney bean leaf strips of 20 mm in diameter were placed and 5 adult female two-spotted spider mites were inoculated and permitted to lay eggs for one day. Next, the adult female mites were removed, and each kidney leaf strip on which eggs were laid was dipped for 15 seconds into medicinal solutions prepared by forming the compounds shown in Table 1 into preparations similarly as in Example 22 and diluting with water containing a surfactant (0.03%) to 300 ppm. After drying on air, the leaf strips were left to stand in a thermostat chamber at 25° C. On 8 days after the treatment, the numbers of non-hatched eggs were examined to determine the egg killing ratio. The results are shown in Table 7.

TABLE 7

| Compound No. | Effect | Compound No. | Effect | Compound No. | Effect |
|---|---|---|---|---|---|
| 2 | 5 | 27 | 5 | 61 | 5 |
| 4 | 5 | 28 | 5 | 62 | 5 |
| 6 | 5 | 29 | 5 | 63 | 5 |
| 7 | 5 | 36 | 5 | 64 | 5 |
| 9 | 5 | 40 | 5 | 65 | 5 |
| 10 | 5 | 41 | 5 | 66 | 5 |
| 11 | 5 | 42 | 5 | 70 | 5 |
| 12 | 5 | 43 | 5 | 71 | 5 |
| 13 | 5 | 44 | 5 | 85 | 5 |
| 14 | 5 | 45 | 5 | 86 | 5 |
| 15 | 5 | 46 | 5 | 92 | 5 |
| 16 | 5 | 51 | 5 | 93 | 5 |
| 18 | 5 | 52 | 5 | 95 | 5 |
| 19 | 5 | 53 | 5 | 96 | 5 |
| 20 | 5 | 54 | 5 | 99 | 5 |
| 21 | 5 | 55 | 5 | 100 | 5 |
| 22 | 5 | 56 | 5 | 101 | 5 |
| 23 | 5 | 57 | 5 | 105 | 5 |
| 24 | 5 | 58 | 5 | 106 | 5 |
| 25 | 5 | 59 | 5 | 107 | 5 |
| 26 | 5 | 60 | 5 | Compound A | 4 |

Example 31

Activity test against adult female citrus red mite (organic phosphorus agent resistance)

On filter papers soaked with water, mulberry leaf strips of 20 mm in diameter were placed and 10 adult female citrus red mites were inoculated. On the other hand, the medicinal solutions prepared by forming the compounds shown in Table 1 into preparations similarly as in Example 22 and diluting with water containing a surfactant (0.03%) to 300 ppm were sprayed each in 5 ml in a spraying tower. After the treatment, each of the strips was left to stand in a thermostat chamber at 25° C., and after 3 days, the numbers of alive and dead mites were examined to determine the acaricidal ratio. The results are shown in Table 8.

TABLE 8

| Compound No. | Effect | Compound No. | Effect |
|---|---|---|---|
| 2 | 5 | 43 | 5 |
| 4 | 5 | 44 | 5 |
| 6 | 5 | 45 | 5 |
| 7 | 5 | 46 | 5 |
| 9 | 5 | 54 | 5 |
| 10 | 5 | 55 | 5 |
| 11 | 5 | 56 | 5 |
| 12 | 5 | 57 | 5 |
| 13 | 5 | 58 | 5 |
| 15 | 5 | 59 | 5 |
| 16 | 5 | 60 | 5 |
| 18 | 5 | 61 | 5 |
| 19 | 5 | 62 | 5 |
| 20 | 5 | 63 | 5 |
| 21 | 5 | 65 | 5 |
| 22 | 5 | 66 | 5 |
| 23 | 5 | 70 | 5 |
| 26 | 5 | 71 | 5 |
| 27 | 5 | 86 | 5 |
| 28 | 5 | 93 | 5 |
| 29 | 5 | 96 | 5 |
| 36 | 5 | 99 | 5 |
| 40 | 5 | 107 | 5 |
| 42 | 5 | Compound A | 5 |

Example 32

Activity test against citrus red mite egg (organic phosphorus agent resistance)

On filter papers soaked with water, mulberry leaf strips of 20 mm in diameter were placed and 5 adult female citrus red mites were inoculated and permitted to lay eggs for one day. On the other hand, the medicinal solutions prepared by forming the compounds shown in Table 1 into preparations similarly as in Example 22 and diluting with water containing a surfactant (0.03%) to 300 ppm were sprayed each in 5 ml in a spraying tower. After the treatment, each of the strips was left to stand in a thermostat chamber at 25° C., and after 10 days, the numbers of non-hatched eggs were examined to determine the egg killing ratio. The results are shown in Table 9.

TABLE 9

| Compound No. | Effect | Compound No. | Effect |
|---|---|---|---|
| 6 | 5 | 44 | 5 |
| 7 | 5 | 45 | 5 |
| 9 | 5 | 46 | 5 |
| 10 | 5 | 54 | 5 |
| 11 | 5 | 55 | 5 |
| 12 | 5 | 56 | 5 |
| 13 | 5 | 57 | 5 |
| 15 | 5 | 58 | 5 |
| 16 | 5 | 59 | 5 |
| 18 | 5 | 60 | 5 |
| 19 | 5 | 61 | 5 |
| 20 | 5 | 62 | 5 |
| 21 | 5 | 63 | 5 |
| 22 | 5 | 65 | 5 |
| 26 | 5 | 66 | 5 |
| 27 | 5 | 70 | 5 |
| 28 | 5 | 71 | 5 |
| 29 | 5 | 86 | 5 |

TABLE 9-continued

| Compound No. | Effect | Compound No. | Effect |
|---|---|---|---|
| 36 | 5 | 96 | 5 |
| 40 | 5 | 99 | 5 |
| 42 | 5 | 107 | 5 |
| 43 | 5 | Compound A | 4 |

Example 33

Control effect against rice blast disease

In pots made of a plastic, soil medium was placed and rice seeds were planted. Cultivation was conducted in a hot house, and on the young seedlings with spreading of main leaf to the 3.5 leaf-stage was sprayed sufficient amounts of the medicinal solutions prepared by forming the compounds shown in Table 1 into preparation similarly as described in Examples 22 and 24 and diluting with water containing a surfactant (0.01%) to 200 ppm. At 48 hours after spraying, a suspension of spores of rice blast disease bacteria (piricularia orizae) was inoculated by spraying and left to stand in a chamber at a temperature of 25° C. and a humidity of 100% for 4 days. The effect of medicine was judged by comparison of the lesion number with that in the non-treated district. Evaluation is shown with no lesion being rated as 5, those with lesion area of 10% or less as compared with the non-treated district as 4 and those wholly afflicted with disease as 0. The results are shown in Table 10.

TABLE 10

| Compound No. | Effect | Compound No. | Effect |
|---|---|---|---|
| 12 | 4 | 53 | 5 |
| 13 | 5 | 54 | 5 |
| 16 | 5 | 55 | 5 |
| 19 | 5 | 56 | 5 |
| 20 | 5 | 57 | 5 |
| 21 | 4 | 58 | 5 |
| 22 | 4 | 59 | 5 |
| 23 | 4 | 60 | 5 |
| 27 | 5 | 61 | 5 |
| 28 | 5 | 62 | 5 |
| 29 | 5 | 63 | 5 |
| 36 | 5 | 65 | 5 |
| 40 | 5 | 66 | 5 |
| 41 | 4 | 77 | 5 |
| 43 | 4 | 86 | 4 |
| 44 | 4 | 92 | 5 |
| 45 | 4 | 99 | 5 |
| 46 | 4 | 100 | 4 |
| 50 | 4 | Compound A | 0 |
| 52 | 4 | Non-treated district | 0 |

According to the present invention, novel alkylaminopyrimidine derivatives having excellent insecticide effect, acaricide effect and fungicide effect can be provided.

We claim:

1. A compound represented by the formula:

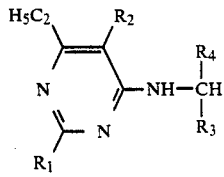

wherein $R_1$ represents a hydrogen atom, a halogen atom, a lower alkyl group, a cycloalkyl group having 3 to 6 carbon atoms, a halogenated lower alkyl group or a phenyl group; $R_2$ represents a halogen atom; $R_3$ represents a hydrogen atom, a lower alkyl group or a cycloalkyl group having 3 to 6 carbon atoms; $R_4$ represents a straight or branched alkyl group having 1 to 20 carbon atoms which may be substituted by at least one selected from the group consisting of 1 to 3 halogen atoms, an alkoxy group having 1 to 15 carbon atoms, a cycloalkylalkoxy group having 4 to 8 carbon atoms, dioxoranyl group, a lower alkoxyalkoxy group, a hydroxy group, a methoxycarbonyl group, a cycloalkyl group having 3 to 6 carbon atoms, a 2-[2-(lower alkoxy)ethoxy]ethoxy group, a 4-t-butylbenzyloxy group, a pyranyloxy group, an imidazol-1-yl group, a triazol-1-yl group, a pyrazol-1-yl group and a substituent Q; where the substituent Q represents —A—B—$R_Q$, in which A represents an oxygen atom or an imino group; B represents a carbonyl group, a thiocarbonyl group or a sulfonyl group; and $R_Q$ represents a lower alkyl group, a cycloalkyl group having 3 to 6 carbon atoms, a halogenated lower alkyl group, an alkoxy group having 1 to 5 carbon atoms, a phenyl group, a 4-methylphenyl group, a phenoxy group, a 3-chloroanilino group, a 2,6-dimethylmorpholin-4-yl group, a 4-methylpiperazin-1-yl group, an imidazol-1-yl group, a triazol-1-yl group, a pyrazol-1-yl group or an amino group substituted by 1 or 2 of lower alkyl groups, or an acid addition salt thereof.

2. A compound according to claim 1, wherein said $R_1$ is a hydrogen atom, a chlorine atom or a methyl group.

3. A compound according to claim 1, wherein said $R_2$ is a chlorine atom or a bromine atom.

4. A compound according to claim 1, wherein said $R_3$ is a methyl group, an ethyl group, an isopropyl group or a cyclopropyl group.

5. A compound according to claim 1, wherein said $R_4$ is a pentyl group, a hexyl group, a heptyl group, an octyl group, a nonyl group, a 8-methylnonyl group, a decyl group, a 6-chlorohexyl group, a 6,6-difluorohexyl group, a 6-hydroxyhexyl group, a 7-hydroxyheptyl group, a 6-methoxyhexyl group, a 6-isopropoxyhexyl group, a 6-cyclopropylmethoxyhexyl group, a 7-methoxyheptyl group, a 6-(2-ethoxyethoxy)hexyl group, a 6-(1-ethoxyethoxy)hexyl group, a 7-(2-ethoxyethoxy)heptyl group, a 7-(1-ethoxyethoxy)heptyl group, a 5-(1,3-dioxoran-2-yl)pentyl group, a 6-acetyloxyhexyl group, a 6-(pyran-2-yloxy)hexyl group, a 6-(N,N-dimethylcarbamoyloxy)hexyl group, a 6-(N,N-dimethylthiocarbamoyloxy)hexyl group, a 6-methanesulfonyloxyhexyl group or a 6-(imidazol-1-yl)hexyl group.

6. A compound according to claim 1, wherein said compound is a salt of hydrochloric acid, hydrobromic acid, nitric acid, sulfuric acid, phosphoric acid, formic acid, oxalic acid, fumaric acid, adipic acid, stearic acid, oleic acid, aconitic acid, methanesulfonic acid, benzenesulfonic acid or p-toluenesulfonic acid.

7. The compound of claim 1 wherein $R_1$ is H, $R_2$ is Cl, $R_3$ is $CH_3$ and $R_4$ is —$(CH_2)_4CH_3$.

8. The compound of claim 1 wherein $R_1$ is H, $R_2$ is Cl, $R_3$ is $C_2H_5$ and $R_4$ is —$(CH_2)_4CH_3$.

9. The compound of claim 1 wherein $R_1$ is H, $R_2$ is Cl, $R_3$ is $CH_3$ and $R_4$ is —$(CH_2)_5CH_3$.

10. The compound of claim 1 wherein $R_1$ is H, $R_2$ is Cl, $R_3$ is $C_2H_5$ and $R_4$ is —$(CH_2)_5CH_3$.

11. The compound of claim 1 wherein $R_1$ is H, $R_2$ is Cl, $R_3$ is $C_3H_7$ and $R_4$ is $-(CH_2)_5CH_3$.

12. The compound of claim 1 wherein $R_1$ is H, $R_2$ is Cl, $R_3$ is cyclopropyl and $R_4$ is $-(CH_2)_5CH_3$.

13. The compound of claim 1 wherein $R_1$ is H, $R_2$ is Cl, $R_3$ is $CH_3$ and $R_4$ is $-(CH_2)_6CH_3$.

14. The compound of claim 1 wherein $R_1$ is H, $R_2$ is Cl, $R_3$ is $C_2H_5$ and $R_4$ is $-(CH_2)_6CH_3$.

15. The compound of claim 1 wherein $R_1$ is H, $R_2$ is Cl, $R_3$ is cyclopropyl and $R_4$ is $-(CH_2)_6CH_3$.

16. The compound of claim 1 wherein $R_1$ is H, $R_2$ is Cl, $R_3$ is $C_2H_5$ and $R_4$ is $-(CH_2)_7CH_3$.

17. The compound of claim 1 wherein $R_1$ is H, $R_2$ is Cl, $R_3$ is $C_3H_7$ and $R_4$ is $-(CH_2)_7CH_3$.

18. The compound of claim 1 wherein $R_1$ is H, $R_2$ is Cl, $R_3$ is $i$-$C_3H_7$ and $R_4$ is $-(CH_2)_7CH_3$.

19. The compound of claim 1 wherein $R_1$ is H, $R_2$ is Cl, $R_3$ is cyclopropyl and $R_4$ is $-(CH_2)_7CH_3$.

20. The compound of claim 1 wherein $R_1$ is H, $R_2$ is Cl, $R_3$ is $C_2H_5$ and $R_4$ is $-(CH_2)_7CH-CH_3)_2$.

21. The compound of claim 1 wherein $R_1$ is H, $R_2$ is Cl, $R_3$ is $CH_3$ and $R_4$ is $-(CH_2)_8CH_3$.

22. The compound of claim 1 wherein $R_1$ is H, $R_2$ is Cl, $R_3$ is $C_2H_5$ and $R_4$ is $-(CH_2)_8CH_3$.

23. The compound of claim 1 wherein $R_1$ is H, $R_2$ is Cl, $R_3$ is cyclopropyl and $R_4$ is $-(CH_2)_8CH_3$.

24. The compound of claim 1 wherein $R_1$ is H, $R_2$ is Cl, $R_3$ is $C_2H_5$ and $R_4$ is $-CH_2)_9CH_3$.

25. The compound of claim 1 wherein $R_1$ is H, $R_2$ is Cl, $R_3$ is $C_2H_5$ and $R_4$ is $-(CH_2)_{11}CH_3$.

26. The compound of claim 1 wherein $R_1$ is H, $R_2$ is Cl, $R_3$ is $CH_3$ and $R_4$ is $-(CH_2)_7CH_3$.

27. The compound of claim 1 wherein $R_1$ is H, $R_2$ is Br, $R_3$ is $CH_3$ and $R_4$ is $-(CH_2)_8CH_3$.

28. The compound of claim 1 wherein $R_1$ is H, $R_2$ is Cl, $R_3$ is $CH_3$ and $R_4$ is $-(CH_2)_2CH(CH_3)C_3H_7$.

29. The compound of claim 1 wherein $R_1$ is H, $R_2$ is Cl, $R_3$ is $C_2H_5$ and $R_4$ is $-(CH_2)_5CH_2Cl$.

30. The compound of claim 1 wherein $R_1$ is H, $R_2$ is Cl, $R_3$ is $C_2H_5$ and $R_4$ is $-(CH_2)_7CH_2Cl$.

31. The compound of claim 1 wherein $R_1$ is H, $R_2$ is Cl, $R_3$ is $C_2H_5$ and $R_4$ is $-(CH_2)_5CHClCH_2CH_2CH_3$.

32. The compound of claim 1 wherein $R_1$ is H, $R_2$ is Cl, $R_3$ is H and $R_4$ is $-(CH_2)_4CH_2F$.

33. The compound of claim 1 wherein $R_1$ is H, $R_2$ is Cl, $R_3$ is $C_2H_5$ and $R_4$ is $-(CH_2)_5CH_2F$.

34. The compound of claim 1 wherein $R_1$ is H, $R_2$ is Cl, $R_3$ is $C_2H_5$ and $R_4$ is $-(CH_2)_7CH_2F$.

35. The compound of claim 1 wherein $R_1$ is H, $R_2$ is Cl, $R_3$ is $C_2H_5$ and $R_4$ is $-(CH_2)_5CHF_2$.

36. The compound of claim 1 wherein $R_1$ is H, $R_2$ is Cl, $R_3$ is $C_2H_5$ and $R_4$ is $-(CH_2)_5CH_2OCH_3$.

37. The compound of claim 1 wherein $R_1$ is H, $R_2$ is Cl, $R_3$ is $C_2H_5$ and $R_4$ is $-(CH_2)_5CH_2OCH(CH_3)_2$.

38. The compound of claim 1 wherein $R_1$ is H, $R_2$ is Cl, $R_3$ is $C_2H_5$ and $R_4$ is $-CH_2-_5CH_2OCH_2$ cyclopropyl.

39. The compound of claim 1 wherein $R_1$ is H, $R_2$ is Cl, $R_3$ is $C_2H_5$ and $R_4$ is $-(CH_2)_7CH_2OCH_3$.

40. The compound of claim 1 wherein $R_1$ is H, $R_2$ is Cl, $R_3$ is $C_2H_5$ and $R_4$ is $-(CH_2)_5CH(OCH_3)CH_2CH_2CH_3$.

41. The compound of claim 1 wherein $R_1$ is H, $R_2$ is Cl, $R_3$ is $C_2H_5$ and $R_4$ is $-(CH_2)_5CH_2OCH_2CH_2OCH_2CH_3$.

42. The compound of claim 1 wherein $R_1$ is H, $R_2$ is Cl, $R_3$ is $C_2H_5$ and $R_4$ is $-(CH_2)_7CH_2OCH_2CH_2OCH_2CH_3$.

43. The compound of claim 1 wherein $R_1$ is H, $R_2$ is Cl, $R_3$ is $C_2H_5$ and $R_4$ is $-(CH_2)_5CH_2OCH(CH_3)OCH_2CH_3$.

44. The compound of claim 1 wherein $R_1$ is H, $R_2$ is Cl, $R_3$ is $C_2H_5$ and $R_4$ is $-(CH_2)_7CH_2OCH(CH_3)OCH_2CH_3$.

45. The compound of claim 1 wherein $R_1$ is H, $R_2$ is Cl, $R_3$ is $C_2H_5$ and $R_4$ is

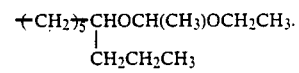

46. The compound of claim 1 wherein $R_1$ is H, $R_2$ is Cl, $R_3$ is H and $R_4$ is

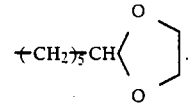

47. The compound of claim 1 wherein $R_1$ is H, $R_2$ is Cl, $R_3$ is $C_2H_5$ and $R_4$ is

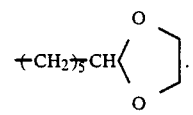

48. The compound of claim 1 wherein $R_1$ is H, $R_2$ is Cl, $R_3$ is $C_2H_5$ and $R_4$ is

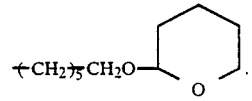

49. An insecticidal, acaricidal and fungicidal composition comprising a carrier and an effective amount of an active ingredient compound represented by the formula:

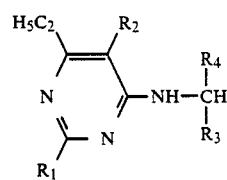

wherein $R_1$ represents a hydrogen atom, a halogen atom, a lower alkyl group, a cycloalkyl group having 3 to 6 carbon atoms, a halogenated lower alkyl group or a phenyl group; $R_2$ represents a halogen atom; $R_3$ represents a hydrogen atom, a lower alkyl group or a cycloalkyl group having 3 to 6 carbon atoms; $R_4$ represents a straight or branched alkyl group having 1 to 20 carbon atoms which may be substituted by at least one selected from the group consisting of 1 to 3 halogen atoms, an alkoxy group having 1 to 15 carbon atoms, a cycloalkylalkoxy group having 4 to 8 carbon atoms, dioxoranyl group, a lower alkoxyalkoxy group, a hydroxyl group, a methoxycarbonyl group, a cycloalkyl group having 3 to 6 carbon atoms, a 2-[2-(lower alkoxy)ethoxy]ethoxy group, a 4-t-butylbenzyloxy group, a pyranyloxy group, an imidazol-1-yl group, a triazol-1-yl group, a pyrazol- 1-yl group and a substituent Q; where the substituent Q represents —A—B—R$_Q$, in which A represents an oxygen atom or an imino group; B represents a carbonyl group, a thiocarbonyl group or a sulfonyl group; and R$_Q$ represents a lower alkyl group, a cycloalkyl group having 3 to 6 carbon atoms, a halogenated lower alkyl group, an alkoxy group having 1 to 5 carbon atoms, a phenyl group, a 4-methylphenyl group, a phenoxy group, a 3-chloroanilino group, a 2,6-dimethylmorpholin-4-yl group, a 4-methylpiperazin-1-yl group, an imidazol-1-yl group, a triazol-1-yl group, a pyrazol-1-yl group or an amino group substituted by 1 or 2 of lower alkyl groups,
or an acid addition salt thereof.

50. A method of treating a locus infected with insects comprising applying to said locus an insecticidally effective amount of a compound as claimed in claim 1.

51. A method of treating a locus infected with acarids comprising applying to said locus an acaricidally effective amount of a compound as claimed in claim 1.

52. A method of treating a locus infected with fungi comprising applying to said locus a fungicially effective amount of a compound as claimed in claim 1.

* * * * *